United States Patent
Weiss et al.

[11] Patent Number: 6,117,505
[45] Date of Patent: *Sep. 12, 2000

[54] STERILIZABLE FLEXIBLE POUCH PACKAGE

[75] Inventors: Mark E. Weiss; Thomas J. Bauer, both of Denver, Colo.; Richard E. Johnson, Appleton, Wis.

[73] Assignees: Whitesell of North Carolina, Inc., High Point, N.C.; American National Can Company, Chicago, Ill.

[*] Notice: This patent is subject to a terminal disclaimer.

[21] Appl. No.: 08/768,286

[22] Filed: Dec. 17, 1996

Related U.S. Application Data

[62] Division of application No. 08/361,321, Dec. 21, 1994, Pat. No. 5,590,777, which is a continuation of application No. 08/025,425, Mar. 1, 1993, Pat. No. 5,459,978.

[51] Int. Cl.$^7$ .............................. B65D 65/40; B65D 81/20
[52] U.S. Cl. ..................... 428/35.2; 428/212; 428/476.1; 428/483; 428/516; 428/519; 206/438; 206/439; 206/484.1; 383/113; 383/200
[58] Field of Search .................. 428/35.2, 35.7, 428/36.8, 516, 519, 212, 476.1, 483; 206/438–441, 484.1; 383/113, 200

[56] References Cited

U.S. PATENT DOCUMENTS

| | | | |
|---|---|---|---|
| 2,997,224 | 8/1961 | Stanuard | 206/439 |
| 3,229,813 | 1/1966 | Crowe, Jr. et al. | 206/439 |
| 3,410,395 | 11/1968 | Sellers | 264/85 |
| 3,496,061 | 2/1970 | Fresheur et al. | 428/461 |
| 3,552,638 | 1/1971 | Quackenbush | 383/210 |
| 3,655,503 | 4/1972 | Stanley et al. | 383/210 |
| 3,761,013 | 9/1973 | Schuster | 206/439 |
| 3,768,725 | 10/1973 | Pilaro | 206/439 |
| 3,926,311 | 12/1975 | Laske | 206/439 |
| 3,930,580 | 1/1976 | Bazell et al. | 206/439 |
| 3,967,729 | 7/1976 | Tanner, II | 206/440 |
| 3,991,881 | 11/1976 | August | 206/439 |
| 4,057,144 | 11/1977 | Schuster | 206/439 |
| 4,168,779 | 9/1979 | Yokokoji et al. | 206/439 |
| 4,270,658 | 6/1981 | Schuster | 206/439 |
| 4,367,816 | 1/1983 | Wilkes | 206/439 |
| 4,407,874 | 10/1983 | Gehrke | 428/35.2 |
| 4,514,965 | 5/1985 | Adachi et al. | 53/553 |
| 4,550,546 | 11/1985 | Railey et al. | 206/439 |
| 4,638,913 | 1/1987 | Howe, Jr. | 206/200 |
| 4,654,240 | 3/1987 | Johnston | 206/524.6 |
| 4,657,804 | 4/1987 | Mays et al. | 428/212 |
| 4,660,721 | 4/1987 | Mykleby | 206/484.1 |
| 4,724,961 | 2/1988 | Shimoyamada et al. | 428/439 |
| 4,778,697 | 10/1988 | Genske et al. | 428/36.8 |
| 4,784,885 | 11/1988 | Corespodi | 428/36.8 |
| 4,857,409 | 8/1989 | Hazelton et al. | 428/494 |
| 4,937,139 | 6/1990 | Genske et al. | 428/349 |
| 4,965,109 | 10/1990 | Tucker et al. | 428/35.7 |
| 5,024,888 | 6/1991 | Hwe et al. | 428/355 EN |
| 5,071,686 | 12/1991 | Genske et al. | 428/35.7 |
| 5,073,436 | 12/1991 | Antonacci et al. | 428/219 |
| 5,089,308 | 2/1992 | Nordness et al. | 428/35.4 |
| 5,093,164 | 3/1992 | Bauer et al. | 428/35.4 |
| 5,108,844 | 4/1992 | Blemberg et al. | 428/518 |
| 5,230,430 | 7/1993 | Kidder | 206/484.1 |
| 5,459,978 | 10/1995 | Weiss et al. | 53/425 |
| 5,590,777 | 1/1997 | Weiss et al. | 206/439 |

*Primary Examiner*—Rena L. Dye
*Attorney, Agent, or Firm*—Larson & Taylor

[57] ABSTRACT

A sterilizable flexible pouch package includes a non-woven barrier web, a perforated plastic intermediate web, and an imperforate plastic upper web. Line heat seals bonding the webs from a cavity into which a sterilizing steam may enter after passing through the barrier and intermediate webs. The line heat seal bonding the upper and intermediate webs is of the delamination failure type. An access opening is provided for insertion of an object to be sterilized into the cavity after which the access opening is sealed, enclosing the object in the cavity. After sterilizing, the package is opened by peeling apart the upper web from the intermediate web which causes a delamination failure of the line heat seal. Preferred materials enable steam sterilization at temperature of 270° F.

7 Claims, 5 Drawing Sheets

STERILIZABLE FLEXIBLE POUCH PACKAGE

This application is a division of application Ser. No. 08/361,321 filed Dec. 21, 1994, now U.S. Pat. No. 5,590,777, which was a continuation-in-part of application Ser. No. 08/025,425 filed Mar. 1, 1993, now U.S. Pat. No. 5,459,978, issued Oct. 24, 1995.

BACKGROUND OF THE INVENTION

1. Field of the Invention

This invention relates to a sterilizable flexible pouch package, to a method of using the pouch, and to apparatus which facilitates use of the pouch. More particularly, the invention relates to such pouches which are sterilizable with steam at high temperatures of up to 270° F. and which are reliably openable, by peeling, after such sterilization. Still more particularly, the invention relates to such packages which are sufficiently large and robust to permit such sterilization of heavy objects, such as a tray bearing medical devices or instruments.

2. Description of Related Art

Various medical instruments and supplies are subjected, prior to use in hospitals, to sterilization treatments such as, for example, sterilization with a sterilizing fluid such as steam, ethylene oxide gas, or hydrogen peroxide plasma, radiation sterilization, and dry-heating sterilization. Ordinarily, the first step in sterilization is to package or wrap the unsterile device before exposing it to a sterilant. Generally, packages are used for sterilization of small, lightweight objects and wrapping is used for sterilization of heavy objects, particularly metal trays in which one or more objects are held. Such trays are usually made of stainless steel and typically weigh from 5 to 16 pounds, and often up to 30 pounds, when loaded.

In all sterilization treatments, there is a general requirement to observe a sterile technique. In the context of packaging or wrapping, it is particularly important that sterile technique be practiced during unwrapping or during opening of a package. For example, sterile technique does not allow a hand or object to contact a sterile item. It is important, therefore, that any flexible wrapping or packaging material have good drapeability, such that it will readily fall away from a sterilized item as the item is unwrapped or as a sterilized package is opened.

A current practice of wrapping a tray for steam sterilization employs a double-layered muslin cloth, commonly known as CSR wrap, that is secured around an unsterile medical device by taping. The wrap permits the steam to penetrate into and out of the interior of the wrap, but acts as a barrier to bacteria and other organisms after sterilization. Normally, a dust cover is also employed in the post-sterilization phase. CSR wrap, however, is prone to fluid strike-through and exhibits tearing with extended use. In addition, steam sterilization methods employing cloth wrap are normally practiced by first unwrapping the sterilized tray, followed by moving the unwrapped tray to an area where the tray contents will be used. Sterile technique requires careful and precise procedures. Accordingly, cloth wrap practice is time consuming and expensive.

An alternative practice replaces muslin wrap with a disposable non-woven CSR wrap that is applied in the same manner, i.e., double-layering of wrap secured by taping and with the use of a dust cover. Although non-woven CSR wraps offer both improved fluid resistance and improved bacterial barrier migration over their cloth counterparts, sterilization practices that use these non-woven materials are still labor intensive and costly.

Steel or plastic self-contained reusable trays fitted with an outer housing that has a replaceable filter have also been employed as sterilization containers. While the steel tray system offers excellent sterility maintenance, it is not an attractive practice for many hospitals because the containers are extremely expensive. Plastic trays, unlike the steel trays, allow for visual inspection and identification of contents by employing a transparent plastic. Although to a lesser degree than the steel counterpart, plastic self-contained sterilization trays are also expensive. Moreover, sterilization trays have considerable mass which gives rise to a problem of sterilant condensate which arises with this method of sterilization.

Sterilization pouches and bags comprised of paper and plastic webs have found wide applications in hospitals. Plastic webs afford easy identification of contents through a transparent plastic web. However, as mentioned above, these applications have been limited to sterilization of small or lightweight objects that are easily packaged.

Kraft paper, both coated and uncoated, is used in such packages for both steam and gas sterilization but is not well suited for heavy objects. Moreover, opening a sealed paper package gives rise to the generation of loose paper fibers, which is undesirable in an operating room or other area where dust is desirably kept to a minimum.

Non-woven materials have been substituted for paper in such packages. For example, sheets of spun-bonded polyolefin such as "Tyvek" are widely used in packages for gas sterilization. "Tyvek" offers greater drapeability and reduced fluid strike-through as compared to Kraft paper. However, Tyvek will not withstand high temperature steam autoclaving, and is not employed as an alternative to CSR wrap in high temperature steam sterilization.

It is obviously important that a sterilizable package be reliably sealed, and that it remain sealed after sterilization such that its sterilized contents remain sterilized for the required time, generally for at least 30 days in the case of hospital instruments. It is also important, however, that the sealed sterilized package is reliably opened without requiring excessive force and without the risk of generating fiber "dust". Peelable heat seals or "peel seals" between opposed plastic webs have been proposed as being suitable for both of these important properties. For example, Sellers, U.S. Pat. No. 3,410,395, discloses a package which comprises a laminar sheet material folded onto itself or assembled with another separately formed sheet or panel and heat sealed to form a pouch. The laminar sheet material comprises a perforated heat sealable film, preferably polyethylene, which is laminated with and bonded to a paper sheet. Steam can penetrate both the paper layer and the perforated film layer to enter the pouch. The heat seal between the facing panels or sheets is said to be peelable and the package is said to be able to withstand steam sterilization and able to be peeled open by the application of a moderate opposing pulling force.

At the present time, most steam sterilization of medical instruments and the like is carried out in hospitals and medical facilities with saturated steam at a temperature of at least 270° F. for a standard three minute, steam exposure. These conditions are referred to hereinafter as "conventional high temperature steam sterilization conditions". The packages disclosed by Sellers are incapable of undergoing sterilization at these conventional high temperature steam sterilization conditions.

Figure 7:
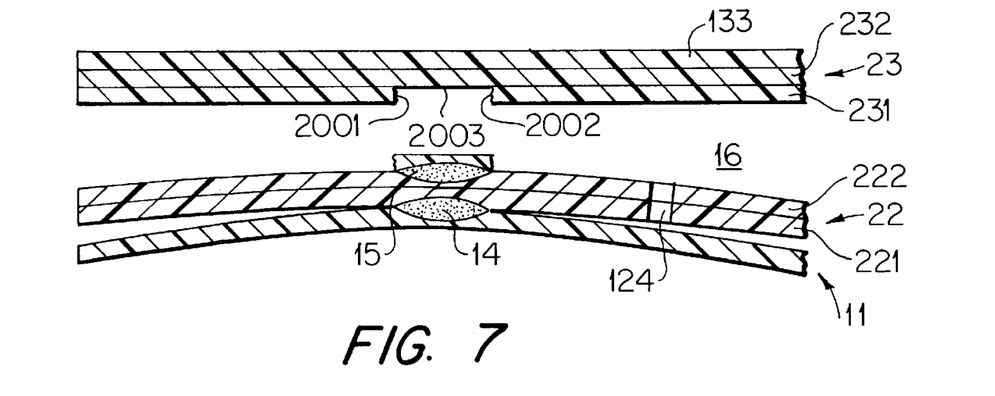
FIG. 7 is a diagrammatic cross sectional view of a portion of an alternative form of a pouch according to the invention.

Wilkes, U.S. Pat. No. 4,367,816 discloses a package which is said to be gas sterilizable, and no mention is made of steam sterilization. This package comprises a low density polyethylene sheet which is heat sealed to a laminar tear strip made up of a gas-permeable paper sheet bonded to a perforated plastic film, the latter film being a sheet of high density polyethylene coated on both sides with a thin layer of a blend of ethylene vinyl acetate and low density polyethylene. The latter layer is heat sealed to the low density polyethylene sheet to form a peelable heat seal. Again, however, the materials will fail when the package is subjected to conventional high temperature steam sterilization conditions. A chevron type package is illustrated in FIG. 7.

Various types of line heat seals which join heat-sealable plastic webs are known in the art. Several of these line heat seals are referred to as "peelable" seals or "peel" seals. A peelable line heat seal is a line heat seal which is openable along the line heat seal by pulling apart heat sealed webs. At least three distinct types of peelable line heat seals are known. In a "true" peel seal, the heat sealed webs separate at their heat sealed interface, with little or no transfer of material from one web to the other. In a "cohesive failure" peel seal, as the heat sealed webs are peeled apart, there is a cohesive failure of only one of the heat sealed webs. The failing heat sealed web tears in a plane which is generally parallel with the plane of the heat seal, Some of the cohesively failed heat sealed web transfers to the web to which it is heat sealed, and some remains behind with the failing heat sealed web. In this type of seal, the strength of the failing heat sealed web is weaker than the heat seal itself. A "delamination failure" or "adhesive failure" peelable heat seal is similar to a cohesive failure seal in that a portion of a failing heat sealed web transfers to the non-failing web. In a delamination failure peel seal, however, the failed web is a lamination, and failure occurs in a predictable location, namely between laminae. In the simplest case, the failing web is a two layer lamination, one layer of which is a heat seal layer which is permanently heat sealed along a permanent line heat seal to the other web. When the heat sealed webs are pulled apart, the failing web readily delaminates in the region of the permanent line heat seal because the permanent line heat seal which bonds the two webs is stronger than the bonding strength between the layers of the failing web. Pulling the webs apart also causes the failing layer to tear at locations just outside and just inside the line heat seal because the bonding strength between the layers of the failing web is stronger than the tear strength of the heat seal layer of the failing web. Thus, the portion of the heat seal layer of the failing web, in the region of the line heat seal, clearly separates by delamination and tearing in a predictable fashion from the layer to which it was laminated, and this separated portion of the failing heat seal layer is transferred to the non-failing web. Thus, failure is generally in a plane which is parallel to the plane of the permanent line heat seal, and there is a transfer of the failed heat sealed layer, in the region of the permanent line heat seal, to the web which did not fail. However, in a delamination failure peel seal, failure proceeds predictably at the interface of the failing lamination and in the region of the permanent line seal.

The present invention relates to sterilizable pouch packages utilizing a delamination failure type of peelable line heat seal.

SUMMARY OF THE INVENTION

It is an object of the invention to provide a flexible sterilizable pouch package which is sterilizable with steam and which is reliably sealed by a delamination failure peelable line heat seal and reliably openable, after steam sterilization, along the peelable seal after sterilization.

It is a further object of the invention to provide such packages which are reliably openable after high temperature steam sterilization.

It is a further object to provide such packages which, when sealed, are sufficiently large and robust to permit sterilization of heavy objects; such as large trays loaded with medical devices and instruments, and which may be reliably opened by pulling apart a peelable line seal without undue force.

It is a further object to provide such packages which, when sealed, are capable of being sterilized under conventional high temperature steam sterilization conditions at a temperature of at least 270° F. for three minutes, and which, after steam sterilization, have a shelf life of at least 30 days.

It is a further object of the invention to provide such packages which permit viewing of the package contents through the packaging material.

It is a further object to provide a method of high temperature sterilization of a sealed pouch in accordance with the invention and it is a further object to provide apparatus for facilitating the loading of objects into a sterilization pouch.

A flexible, steam-sterilizable pouch package according to the invention comprises:

a flexible, sterilization fluid-permeable non-woven lower barrier web;

a flexible impermeable plastic upper web; and a flexible, plastic intermediate web having an interior steam-permeable region;

said intermediate web being bonded to said upper web by a first permanent line heat seal located peripherally outside said, steam-permeable region, said first permanent line heat seal defining limits of a cavity between said upper web and said intermediate web for receiving an object to be sterilized, said first permanent line heat seal extending less than fully peripherally around said permeable region whereby a heat seal-free region of first permanent line heat seal provides an access opening for inserting an item to be sterilized into said cavity;

said intermediate web being bonded to said barrier web by a second permanent line heat seal peripherally outside said steam-permeable region of said intermediate web, said second permanent line heat seal being located such that, when the pouch is fully sealed, sterilizing fluid can penetrate into said cavity only by passing first through said barrier web and thereafter through said permeable region of said intermediate web;

one of said intermediate and upper webs being a multi-layer web having a first heat sealable layer selected from the group consisting of polypropylene, polypropylene copolymers, and mixtures thereof and a core layer bonded thereto selected from the group consisting of polyisobutylene-modified high-density polyethylene (RMHDPE) and a blend of RMHDPE with polypropylene or polypropylene copolymer, and the other of said intermediate and upper webs being heat sealable to the heat sealable layer of said multi-layer web and being heat sealed thereto by said first permanent line heat seal;

the bond strength of said first permanent line heat seal being stronger than the bond strength between said first heat sealable layer and said core layer of said intermediate web, and the bond strength between said first heat sealable layer and said core layer of said multi-layer web being greater than the tear strength of said first heat sealable layer of said multi-layer web, whereby a delamination failure peel seal is present between said intermediate and upper webs in the region of said first permanent line heat seal.

A method of sterilizing an object according to the invention comprises:

(a) providing a flexible steam-sterilizable pouch according to the invention;

(b) placing an object to be sterilized in the cavity of the pouch;

(c) sealing the pouch such that the object to be sterilized is sealed in said cavity and such that sterilizing fluid can penetrate into said cavity only by first passing through the lower web and then through the perforated region of the intermediate web; and (d) sterilizing the sealed pouch with steam.

DEFINITIONS

The expression "delamination failure peel seal" as used herein means a peelable seal which opens as described hereinafter in connection with FIGS. 4–7.

The expression "permanent line heat seal" means a fusion or weld heat seal bonding two webs. The seal extends along a line and has a bonding strength that is greater than either of the bonded webs. An attempt to separate the bonded webs along the seal will result in destruction of at least one of the webs.

The expression "laminated" refers a multi-layer structure in which adjacent layers are bonded over essentially their entire adjacent surfaces, and is used broadly to encompass coextrusions, true laminations of pre-formed sheets bonded to one another either with or without adhesives, and coated layers.

A "barrier" web is a web that is sufficiently porous to steam sterilant for sterilization, and which is an effective barrier against the passage of bacteria.

DESCRIPTION OF PREFERRED EMBODIMENTS

Figure 1:
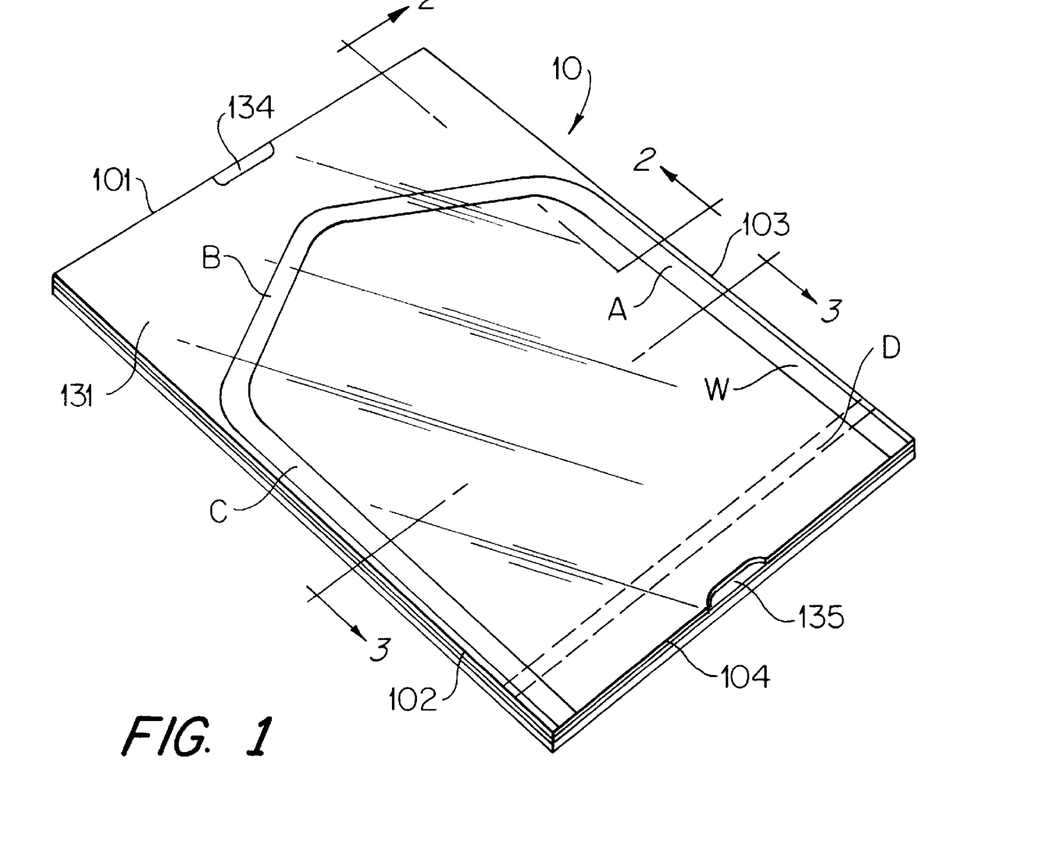
FIG. 1 is a diagrammatic plan view of a first embodiment of a pouch according to the invention.
Figure 2:
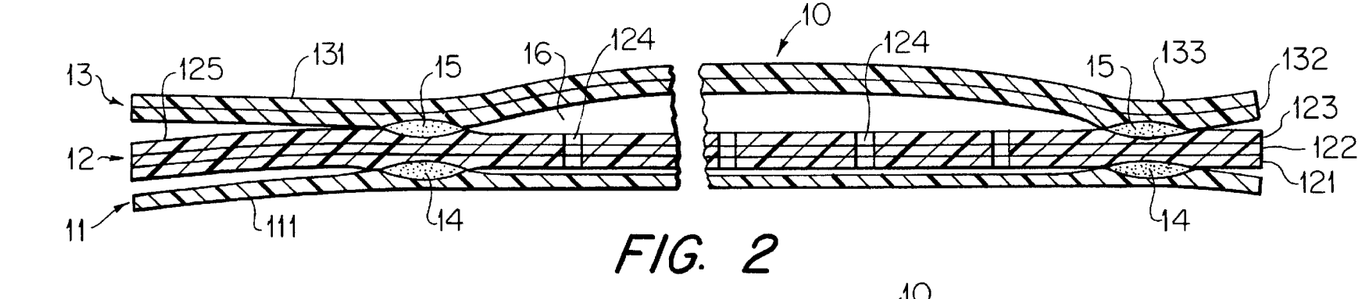
FIG. 2 is a diagrammatic, enlarged, cross sectional view along line 2—2 of FIG. 1.
Figure 3:
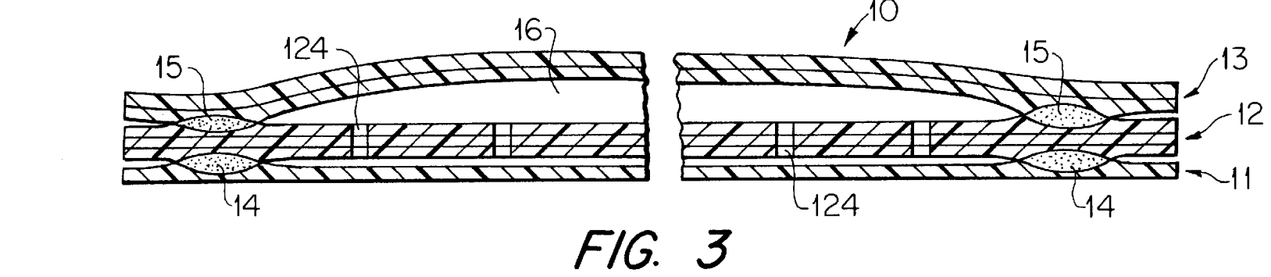
FIG. 3 is a diagrammatic, enlarged, cross sectional view along line 3—3 of FIG. 1.

With reference to FIGS. 1–3, a sterilizable pouch 10 in accordance with the invention comprises a steam-permeable non-woven lower mono-layer web 11, a plastic intermediate tri-layer web 12 and a plastic two-layer upper web 13. While the term "pouch" is used herein, it will be understood that such pouches are also referred to as bags, receptacles, and the like. Lower web 11 is bonded to intermediate web 12 by a fiber-tearing permanent hermetic line heat seal 14. Intermediate web 12 is bonded to upper web 13 by a permanent hermetic line heat seal 15. Both heat seals are provided in regions A, B and C (FIG. 1) of the webs. The terms "lower" and "upper" are used herein in the sense of the drawings and in the sense in which the pouch is normally oriented in use. It is quite possible to use the pouch with what is referred to herein as the "upper web" lowermost. The upper and lower webs are, however, distinct in that the upper web is a fluid-impermeable plastic web which is preferably transparent and forms with the plastic intermediate web a cavity for holding an object to be sterilized. The lower web, on the other hand, is fluid-permeable and may be opaque.

Lower web 11 may be any flexible steam-permeable barrier web which provides an effective barrier against the migration of micro-organisms, particularly bacteria, and which is capable of forming a fiber tearing permanent line heat seal with the intermediate web, the web and the heat seal both preferably being capable of withstanding high steam sterilization temperatures such as steam sterilization at 270° F. Lower web 11 is preferably more drapeable than Kraft paper.

Suitable non-woven material for lower web 11 includes conventional non-woven materials used in the medical field. Paper and some plastic products, such as spun bonded polyolefin or polyester products, are suitable. When sterilization is conducted at relatively low temperature, spun bonded polyethylene barrier fabric, such as "Tyvek", is suitable. For high temperature steam sterilization at 270° F., a suitable material is a non-woven blend of spunlaced polyester and cellulosic material sold under the trademark "Sontara". Other useful non-woven Sontara products are made up entirely of non-woven polyester or non-woven polyester blended with rayon. A particularly preferred high-temperature material is a drapeable trilaminate polypropylene barrier fabric such as "Securon" (Fiberweb Group) which has an inner melt-blown polypropylene core layer between outer spun-bonded polypropylene layers.

One of the principal advantages of the invention is in the ability to use the pouch, for steam-sterilization heavy objects weighing up to about thirty pounds. Lower web 11 together with intermediate web 12 will support the weight of an object in the pouch. If web 12 is sufficiently strong to bear the entire load, the load-bearing strength of web 11 is not of particular concern. Quite the opposite is true, of course, if web 12 has little load bearing strength. The weight of web 11 needed to achieve the desired strength will, of course, depend on the strength-to-weight characteristics of the web. In view of the foregoing, it will be understood that when considering load-bearing properties only, the weight (i.e., the thickness) of web 11 can vary quite widely. In general, it is preferred that webs 11 and 12 together are sufficiently strong to support the full weight of any object for which a particular pouch is designed to accommodate. Since bottom layer 11 is an outer layer, it is preferably abrasion and tear resistant and has the general qualities required for maintenance of sterility. Web 13 is preferably also sufficiently strong to bear the entire load of objects in the pouch.

Web 11 should be sufficiently permeable to steam to permit sterilization to be accomplished under conventional high temperature conditions, for instance, steam sterilization with saturated steam at 270° F. for a three minute cycle. Steam sterilization under these conditions is indicated by a standard test in which test microorganism are killed to a suitable specified level such as the $10^{-6}$ level. Conventional and widely available web materials of the type mentioned above have more than adequate porosity.

Barrier web 11 must also constitute an adequate barrier against the migration of bacteria. Adequacy in this respect is measured by measuring shelf-life of a sterilized package. Adequate barrier properties are indicated when a sterilized objects sealed package stored at room temperature under ambient conditions, remains sterile after at least 30 days. It will be understood that this property may also be involved in determining the required weight of web 11. Thus, where strength considerations may allow a very light weight web, microbial barrier properties may require a heavier weight. Securon barrier fabric having a weight of from 1 to 4 ounces per square yard is preferable for high temperature steam sterilization. Conventional and widely available webs of the materials mentioned above are readily available in weights which give clearly adequate strength and microbial barrier properties.

Microbial barrier properties may be enhanced by incorporating one or more anti-microbial agents such as a bactericide into the barrier web. For example, web 11 may be impregnated with a solution of a quaternary ammonium bactericide and then dried to incorporate the bactericide in the web. Similarly, web 11 may be treated to enhance its water repellency. For example, the web may be treated with a conventional polysiloxane water repellant.

Intermediate web 12 is a flexible heat sealable plastic web having a bottom layer 121, a core layer 122, and a top layer 123. The terms "top" and "bottom" are again used in a sense of the normal orientation of the pouch in use, that is, with the pouch disposed generally horizontally with upper web 13 uppermost as shown in FIGS. 2 and 3. Top layer 123 of web 12 is a plastic layer which forms a hermetic permanent line heat seal 15 with upper web 13, and is preferably polypropylene or a polypropylene copolymer such as a propylene-ethylene copolymer, or blends thereof. Preferred propylene-ethylene copolymers contain ethylene in the range of up to 6%, preferably 1–5%. Bottom layer 121 of web 12 is a plastic which forms a hermetic permanent line heat seal 14 with barrier web 11. Suitable plastic materials include polypropylene, or propylene copolymers, or blends of polypropylene and a compatible polymer such as polyisobutylene-modified high density polyethylene referred to herein as "RMHDPE". A blend of polypropylene with from 20–80% by weight and preferably 30–70% by weight RMHDPE based on the weight of the blend, is preferred. A preferred RMHDPE contains from 5 to 60%, more preferably 20–40% and most preferably 25–35% by weight of polyisobutylene (PIB) based on the weight of the RMHDPE.

Core layer 122 is a polyisobutylene-modified high density polyethylene (RMHDPE) preferably containing from 5 to 60% by weight of PIB and more preferably containing from 20–40% PIB, and most preferably containing 25–35% PIB, based on the weight of the RMHDPE. Inorganic additives such as calcium carbonate, mica, silica, talc or barium sulphate may be added to one or more of the layers of the intermediate web.

Figure 4:
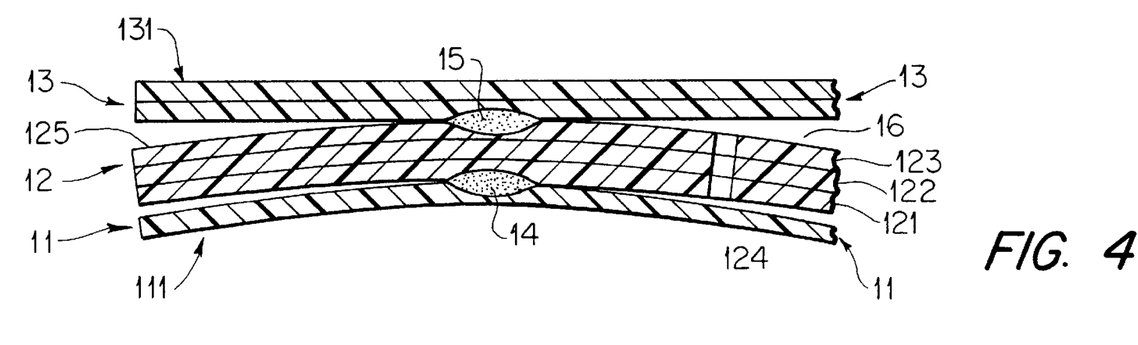
FIGS. 4–6 are diagrammatic cross sectional views showing, sequentially, the peeling open of a delamination failure peel seal of the pouch of FIGS. 1–3.
Figure 5:
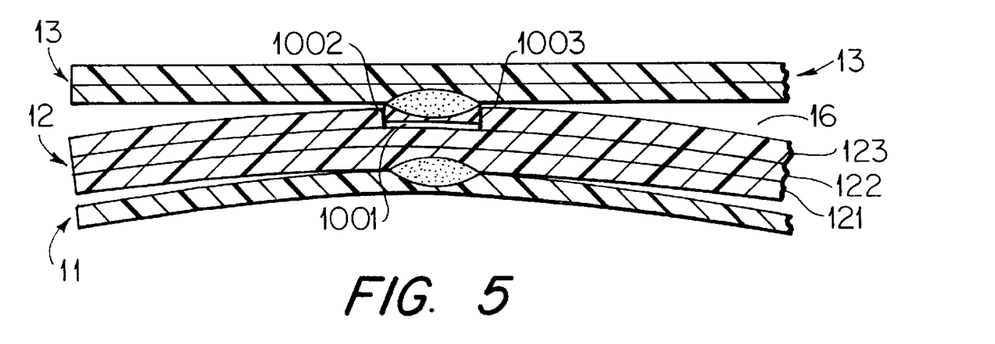
Figure 6:
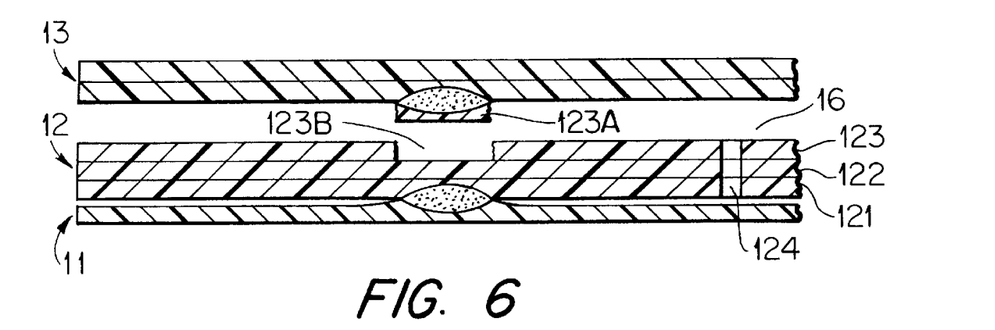

Delamination failure of the peelable line heat seal of the pouch package of FIGS. 1–3 is shown in FIGS. 4–6. The peelable line heat seal depicted in FIGS. 4–6 is between upper web 13 and intermediate web 12 in line seal region "B" of FIG. 1. This peelable seal is opened by grasping flange area 131 of upper web 13 with one hand while simultaneously grasping flange areas 111 and 125 of webs 11 and 12 with the other hand, and pulling apart. Permanent line seal 15 is stronger than the bonding strength between heat seal layer 123 and core layer 122 of intermediate web 12 which in turn is stronger than the tear strength of heat seal layer 123. Accordingly, pulling apart web 13 from webs 11 and 12 causes heat seal layer 123 to delaminate in an area 1001 in the region of heat seal 15 and to tear in areas 1002 and 1003 just outside and inside of the region of line heat seal 15 as shown in FIG. 5. As shown in FIG. 6, a portion 123A of heat seal layer is separated from core layer 122 in the region of heat seal 15, and is transferred to upper web 13. The gap 123B in web 12 and portion 123A adhered to web 13 provide visual indication of the proper functioning of the delamination failure heat seal. Delamination failure of the peel seal in the manner just described is ensured by the relative strengths of the materials and bonds making up the seal.

In an alternative embodiment, delamination of the peelable seal occurs in the upper web. This is illustrated in FIG. 7 which is a diagrammatic cross sectional view corresponding to FIG. 6 except that in this embodiment, delamination occurs in the upper web. The pouch is generally similar to the pouch of FIGS. 1–3 and like portions are designated by like numerals. The pouch illustrated in FIG. 7 includes a lower web 11, an intermediate web 22, and an upper web 23, with cavity 16 between the intermediate and upper webs. Permanent line heat seals 14 and 15 are provided as described above. In this embodiment, however, upper web 23 is a three-layer web with its heat seal layer 231 and core layer 232 corresponding, respectively, to heat seal layer 123 and core layer 122 of the pouch of FIGS. 1–3. Permanent line heat seal 15 is formed between layers 231 and 222. Intermediate web 22 is heat sealable, by permanent line heat seal 14, to barrier web 11 and may include a heat seal layer 221 for this purpose. Intermediate web 22 may also include a core layer for strength or for purposes of promoting adhesion between layers 221 and 222. Intermediate web 22 may also be a mono-layer, provided that it is heat sealable via permanent line heat seals 14 and 15, to the upper and lower webs.

Accordingly, as the pouch of this embodiment is pulled open as described above in connection with FIGS. 4–6, delamination failure involves tearing of heat seal layer 231 at 2001 and 2002 and delamination in region 2003, thus creating access to cavity 16.

Referring again to FIGS. 1–3, upper web 13 is superposed directly above top heat seal layer 123 of web 12 and lower web 11 is positioned directly below bottom heat seal layer 121 of web 12. The three layers (121, 122 and 123) of web 12 are bonded together at least at marginal regions of the layers and are preferably at least substantially coextensive and bonded together across their entire mutually adjacent surfaces. Bonding can be effected by an adhesive seal, by a heat seal, by coextrusion, by lamination of discrete films, etc. Bonding between core layer 122 and bottom layer 121 may be effected by means of one or more tie layers interposed between the layers. Such tie layers may be bonded to the respective layers in any of the ways just mentioned. However, it is critical in this embodiment of the invention that the bonding of the upper web layer 13 to the top layer 123 of intermediate web 12 forms a reliable delamination failure seal peel with delamination occurring only in the area of the line heat seal, and only between heat seal layer 123 and core layer 122 of web 12.

The relative permanent heat seal strengths, the tear strength of the failing heat seal layer, and the strength of the bond between the failing laminae can be achieved by conventional means known in the art such as by selection of the plastic material, by adjustment of the thickness of the layers in question, or by adjusting the conditions of making permanent line seals 14 and 15 such as by adjusting platen temperature, dwell time, or platen pressure, by using opposing heated platens, by repeating the heat sealing operation, and the like.

The plastic material of web 12 in essentially impervious to steam and must be rendered pervious such as by being perforated as at 124 in FIGS. 2–3 to permit the sterilizing fluid to pass through the web. The size and number of perforations 124 may vary widely, the only requirement being to ensure adequate passage of steam for sterilization. It is not required that web 12 have barrier properties. It is preferred to provide relatively large perforations of about ¼ inch in diameter over the surface of the intermediate web 12. However, the size and number of the perforations can vary widely. For example, perforations of about 0.05 mm to 1 mm in diameter spaced apart about 0.5 to 5 mm are suitable, as are ¼" circular perforations spaced apart about 1 to 4 inches. Perforations much smaller than the width of line heat seals 14 and 15 will not affect the integrity of the heat seals and may extend into the line heat seal regions of web 12. Large perforations, however, should be confined to regions peripherally inside the line heat seals for seal integrity.

The weight or thickness of intermediate web 12 can vary widely, and considerations similar to those mentioned above are applicable to web 12 although the abrasion and tear resistance are not as important as in an outer web. Thickness must of course be sufficient to retain integrity during normal handling, but increasing thickness significantly beyond that point will general increase costs and is therefore undesirable. In general, an overall thickness of the intermediate web is suitably from 1 to 10 mils, and preferably from 2 to 7 mils (one mil=0.001 inch). The intermediate web is usually a multi-layer web and, in that event, the thickness of each layer of the web is suitable from 10 to 80% of the web thickness.

Bottom layer 121 is heat sealed at line seal 14 to lower web 11 at a location peripherally outside of the perforated region of web 12. In the embodiment illustrated in FIGS. 1–3, line heat seal 14 is located at marginal regions A, B, and C adjacent to three sides of the pouch package.

Due to considerations of sterile technique, it is preferred that marginal regions A and C of the line heat seals extend near or at outside side edges 102 and 103 of the pouch. However, it is not necessary that the heat seal be at the outside side edge of the pouch. In fact, it is preferred for processing purposes that heat seals in regions A and C are located just inside the outer edges 102 and 103. Therefore, the terms "margin", "marginal area" and "marginal region" and the like as used herein are intended to include regions both at the edge of a web as well as to regions which are near to such an edge.

In a preferred embodiment as illustrated in FIG. 1, portion B of the heat seal is spaced peripherally inside end 101 of the pouch in order to provide flange areas 111, 125 and 131, respectively, in webs 11, 12, and 13, the flange areas being peripherally outside of the seal area. The flange portions are used in opening a sealed pouch as described above. Other portions of the heat seal, such as regions A and C which extend along sides 102 and 103 of the pouch indicated in FIG. 1, are just inside the edges of the pouch in order to facilitate processing while minimizing the amount of web material required for a given pouch.

Heat seals 14 and 15 are permanent line heat seals designed to be retained intact during normal use of the pouch. The strength of permanent heat seal 14 is greater than the tear strength of the weaker of the two webs which it seals and is, as aforementioned, significantly stronger than the bond strength between heat seal layer 123 and core layer 122 of intermediate web 12.

In a preferred embodiment, the perforated region of web 12 extends over at least a major portion of the surface area of the web and is more preferably substantially coextensive with the surface area of web 12 which forms a wall of cavity 16. However, the perforated region of web 12 may be considerably smaller, the major consideration being adequate porosity to sterilizing fluid during sterilization. Since the perforated region of web 12 need not be coextensive with web 13, it will be readily apparent that it is necessary only that web 11 be sized to cover and enclose the perforated region of web 12, with heat seal 14 being located peripherally outside of the perforated region. A structure of that type will reduce the amount of material needed for web 11, but may complicate the method of making the pouch.

Top layer 123 of web 12 is heat sealed at permanent line heat seal 15 to upper web 13 at a location peripherally outside of cavity 16 of the pouch. In a preferred embodiment, heat seal 15 is provided in the same regions A, B and C as heat seal 14 and is therefore superposed directly over and is both substantially coextensive with and in substantial registration with heat seal 14. Heat seal 15 is a permanent seal which has a bond strength greater than the laminating strength between layers 123 and 122 of intermediate web 12 and greater than the tear strength of heat seal layer 123. Thus, when upper web 13 is pulled away from webs 12 and 11, layers 123 and 121 delaminate and layer 123 tears, as described above, in the area of seal 15.

Upper web 13 is a flexible, steam impermeable plastic web which is heat sealable to top layer 123 of intermediate web 12 and is preferably transparent to permit viewing of objects located in cavity 16. Upper web 13 has a heat sealable bottom layer 132 bonded to its top layer 133. The terms "top" and "bottom" are again used in the sense of normal use of the package with layer 133 uppermost and with bottom layer 132 superposed directly above cavity 16 and layer 123 of web 12 as shown in FIGS. 1–3. As in the case of web 12, bonding between layers 132 and 133 is preferably effected at least substantially across the entire web as in a lamination or a coextrusion. In a preferred embodiment, web 13 is a lamination. However, bonding of the layers can be effected by an adhesive or by the use of one or more tie layers, and such bonding need not be effected over the entire surface area of the layers.

The main requirements of web 13 are that it is capable of forming with layer 123 of web 12 a permanent line heat seal having a relative bond strength as described above. In preferred embodiments of the invention, More importantly, these relative bond or seal strengths are retained after conventional high temperature steam sterilization such as steam sterilization for a three minute cycle at a temperature of 270° F.

Layer 133 adds strength to upper web 13. Suitable plastics include nylon, including cast nylon which is preferred for high temperature steam sterilization, biaxially oriented nylon (which becomes very distorted under high temperature steam sterilizing), and polyester, such as polyethylene terephthalate. Heat seal layer 132 of upper web 13 is preferably polypropylene or a propylene copolymer such as an ethylene copolymer, or blends of such copolymers with polypropylene as described above. The thickness of top layer 133 is chosen to impart sufficient strength and toughness to web 13 to permit handling of a sealed pouch containing a relatively heavy loaded tray as mentioned above. In general, a thickness of at about 0.3 to 8 mil is suitable and about 0.5 to 6 mil is preferred. Since an increase in thickness will result in less flexibility and increased cost, thickness is preferably kept to the minimum required for sufficient strength and toughness. The thickness of heat seal layer 132 of upper web 13 is suitably 0.5 to 6 mil and preferably 2 to 4 mil.

The seal width of a pouch in accordance with the invention may vary considerably, but is preferably from 1/8" to 1", more preferably from 1/8" to 3/4, and optimally approximately 1/4". The width of the seal may be, but need not be, substantially the same throughout its length. For example, it may be desirable to have a wider or narrower seal in chevron region B than in regions A and C.

After sterilization, the package is preferably opened manually by grasping with one hand flange area 131 of upper web 13 and grasping flange areas 111 and 125 of webs 11 and 12 simultaneously with the other hand, and then pulling apart. Drapeability, which imbues a web with the ability to fall away as it is peeled away, is an important attribute, and preferred webs of the present invention have a high degree of drapeability. Grasping the flanges is facilitated by providing a cut-out area 134 in upper web 13 or by providing a similar cut out in webs 11 and 12. For a rectangular type of pouch as shown in FIG. 1, it is preferred to provide region B as a conventional chevron at one of the narrower ends of the pouch, the angle included at the apex of the chevron preferably being from 110 to 150°, and more preferably from 130 to 150°.

The delamination failure peel seal preferably extends along substantially the full length line of permanent line heat seal 15. However, it is only required that the peel seal extends a distance along the line heat seal such that when the peel seal portion of the heat seal is fully peeled open, the contents of cavity 16 are readily accessible. For example, it is often desirable to make-permanent seals between webs 12 and 13 in the regions of line heat seal A and C which are at the end of the pouch and adjacent to the access opening of the pouch. A permanent seal at this point will prevent undesirable premature peeling apart of webs 12 and 13 when an object is inserted into the pouch.

Line heat seal 15 defines the outer limits of cavity 16 for holding one or more items to be sterilized. Line heat seal 15 does not, however, extend completely around cavity 16 as it is necessary to provide the pouch with an access opening to permit insertion into cavity 16 of an object to be sterilized. Heat seal 15 is therefore omitted from at least one marginal region of the pouch to provide access between webs 12 and 13 into cavity 16. Preferably, a single access opening in seal 15 is provided. In the case of a rectilinear package such as shown in FIG. 1, the access opening is preferably provided at an end 104 of the pouch remote from end 101 which is first employed in opening the sealed pouch. In the preferred embodiment shown in FIGS. 1–7, the access opening extends fully across end 104 between seal regions A and C. However, the access opening can be extended for a lesser distance and, as mentioned above, it is not required that the peelable heat seals extend fully to end 104 in regions A and C.

In a preferred embodiment, line heat seal 14 is also omitted in the region where the access opening is provided. Thus, in the pouch illustrated in FIGS. 1–7, line heat seal 14 is provided directly below line heat seal 15 in regions A, B and C, but line heat seals 14 and 15 are both omitted from end 104 of the pouch. On the other hand, it is advantageous that webs 11 and 12 are bonded together at ends 101 and 104 to facilitate handling, both when inserting an object into cavity 16 and when peeling apart web 13 from webs 11 and 12.

The pouch is preferably rectilinear in plan view and is more preferably rectangular as illustrated. However, it will be readily understood that the pouch package can be square, oval, round, and of virtually any desired shape.

The pouch has particular utility in steam sterilization in a hospital or other facility, of trays loaded with one or more re-useable metal instruments and the like. The trays as well as the instruments are usually metal and are quite heavy. The trays are typically made of stainless steel, are rectangular, having a length of 7 to 21 inches, a width of 3 to 13 inches, a height of 2 to 4 inches, and a weight, when loaded, of from 5 to 16 or even up to 30 pounds. For use with such trays, a pouch in accordance with the present invention has a length of about 20 to 36 inches, and a width of 10 to 20 inches. Such trays are commonly sterilized at the current time only after a careful and time-consuming wrapping procedure and it is also necessary to carry out a careful unwrapping procedure before the sterilized instruments can be used. As mentioned above, sterile technique must be maintained. Trays wrapped and unwrapped in this manner can be successfully sterilized under conventional high temperature autoclave conditions at 270° F., but the procedure is time-consuming and exacting. The present pouch avoids the conventional wrapping and unwrapping procedure in that one simply inserts loaded trays into cavity 16, seals the pouch, and inserts the sealed pouch in a steam autoclave for sterilization with saturated steam for the prescribed time. Preferred pouches in accordance with the invention are sterilizable with steam under high temperature steam sterilizing conditions. If desired, the pouch can be provided with a conventional indicator means for showing that the sterilization is complete. Suitable indicators include inks and tapes. After sterilization is complete, the sterilized pouch package may be stored until ready for use. Shelf life of a sterilized pouch package is comparable to that of the conventional wrapped trays, and is at least about 30 days. When ready for use, the sterilized pouch package is simply opened manually by grasping the flange areas to open the delamination failure peel seal as described above. The two webs which surround cavity 16 have smooth plastic surfaces which, together with the reliable peeling open of the peel seal, virtually eliminate the generation of fiber fragments or dust. Thus, the present invention provides an alternative to the conventional CSR wrap method of steam sterilization of large heavy objects.

After an object to be sterilized has been inserted into cavity 16, the package is sealed. It is, of course, required to seal the opening, if present, at package end 104 between webs 11 and 12 as well as the access opening between webs 12 and 13. This can be accomplished in any of several ways, such as by providing the package with an adhesive coating or tape or by heat sealing. The pouch illustrated in FIG. 1, for example, is readily heat sealed in marginal region D. Heat sealing can be readily effected by the user by employing conventional and simple heat sealing equipment. Sealing in that event would preferably be conducted to simultaneously provide a permanent line heat seal in region D between webs 12 and 13 and between webs 12 and 11.

Figure 8:
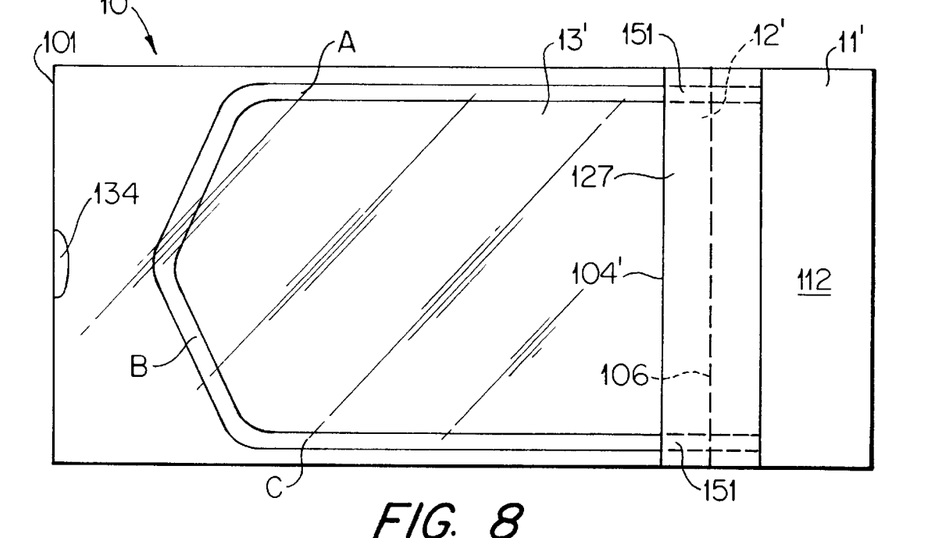
FIG. 8 is a diagrammatic plan view of a second embodiment of a pouch according to the invention.
Figure 9:
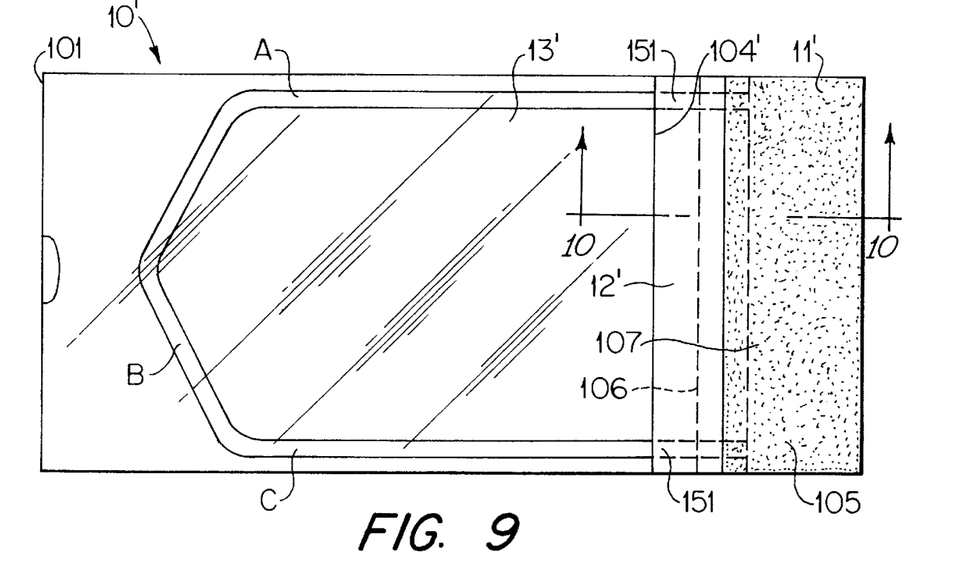
FIG. 9 is a diagrammatic plan view of the pouch of FIG. 8 with an adhesive strip attached thereto.

In a preferred embodiment, the pouch is sealed by an adhesive strip provided on the pouch as illustrated in pouch 10' in FIGS. 8–11. Pouch 10' is the same as pouch 10 of FIGS. 1–3 except that in FIGS. 1–3, webs 11, 12 and 13 are of the same length whereas in FIGS. 8–11, webs 11', 12' and 13' are of progressively decreasing length. At end 101 of the pouch, the ends of webs 11', 12; and 13' are in registration. At the opposite end of the pouch, intermediate web 12' extends outwardly beyond the end of upper web 13' forming a first flap region 127 in web 12', and lower web 11' extends outwardly beyond the end of intermediate web 12' forming a second flap portion 112' in web 11'. With the webs in registration as shown in FIGS. 8 and 9, a length of double sided adhesive tape 105 is applied across the full width of the pouch in position to seal the outer edge of flap portion 127 of intermediate web 12 to the upper surface of flap portion 112' of lower web 11'. In this embodiment permanent line heat seal 14 in areas A and C preferably extends in regions 151 beyond the outer end of upper web 11' to the outer end of intermediate web 12'.

Figure 10:
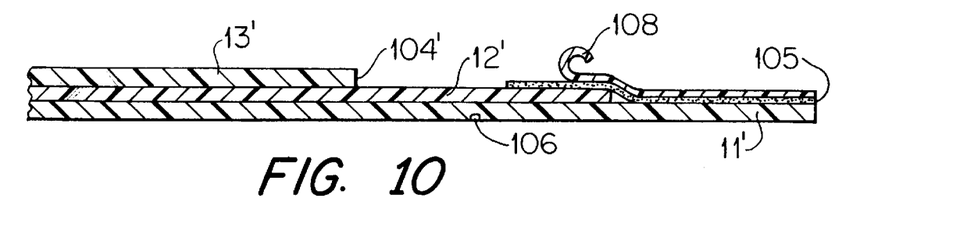
FIG. 10 is an enlarged, diagrammatic cross sectional view along the line 10—10 of FIG. 9.
Figure 11:
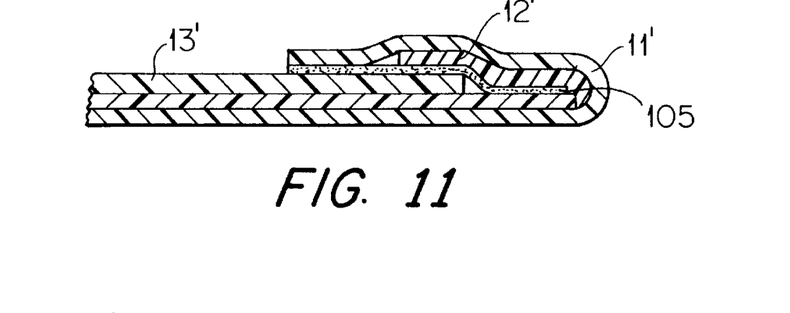
FIG. 11 is an enlarged, diagrammatic cross sectional view similar to FIG. 10, but showing the pouch after folding an end thereof.

Adhesive stock for adhesive strip 105 is widely available and preferably includes a removable release strip 108. The adhesive strip preferably covers substantially all of flap portion 112' of lower web 11' and about 30 to 60% of flap portion 127 of intermediate web 12'. A fold line 106 is preferably provided across flap 127 at a point located between edge 104' of upper web 11' and the inner edge 107 of adhesive strip 105. To seal the access opening of cavity 16 between the top and intermediate webs, the pouch is folded at fold line 106 to bring the outer end of the adhesive strip and lower web 14' up over the upper surface of upper web 13' into the position shown in FIG. 8. The adhesive strip is pressed downwardly and adhered to the upper surfaces of the top and intermediate webs thus sealing the access opening of cavity 16. It is preferred to seal the pouch in the manner depicted in FIGS. 8–11 and in that event the adhesive strip is preferably provided on the pouch as shown in FIGS. 8–10 during the manufacturing process. However, it will be understood that there are several ways in which the pouch may be sealed.

As mentioned above, the invention has particular utility in the sterilization of objects carried in trays weighing, when loaded, up to 30 pounds or more. Such trays are usually fabricated of stainless steel, typically 10"×20"×3", with the bottom of the tray being a screen positioned about ½–¾ inches above the bottom of the tray sides to maintain the tray bottom, i.e., the screen, above a horizontal surface on which the tray is placed.

Figure 14:
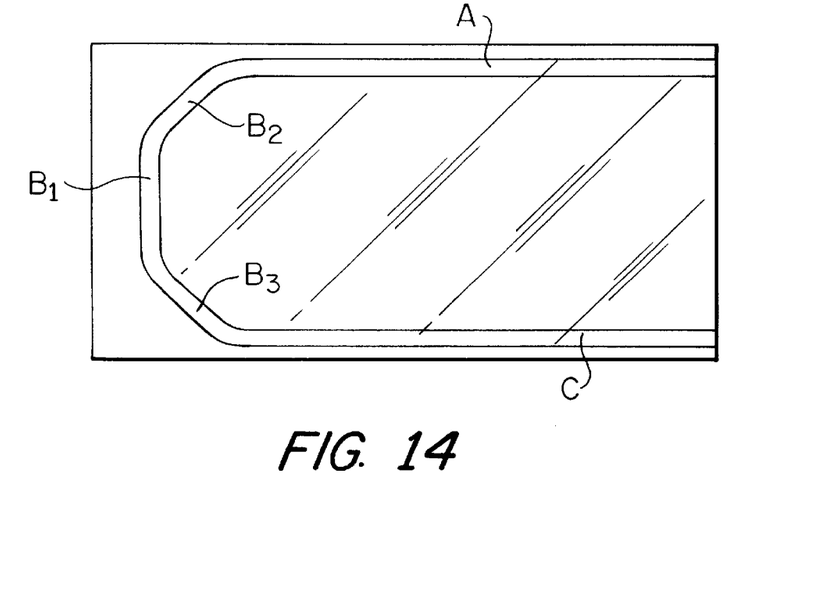
FIG. 14 is a diagrammatic plan view of a third embodiment of a pouch according to the invention.

While a chevron style pouch package is preferred in many instances, other arrangements of the permanent line heat seals in region B are also useful and may be preferred in some instances. For example, region B of the line heat seal may be arcuate or rectilinear. For large packages, there is a tendency for the user to peel apart from a corner of the package rather than from the center. For such large pouches, it is preferred to provide a line heat seal in region B having a "barn roof" configuration such as illustrated in FIG. 14, having a generally flat central region B₁ and sloped regions B₂, B₃ at either side of the flat region extending outwardly and downwardly toward the edges of the package, preferably at a relatively sharp angle of from 35–55°, and more preferably about 45°, with each sloped region occupying about 20–40% of the length of the line heat seal in region B. When region B is of the chevron type, the sloping sides of the chevron are preferably inclined downwardly and outwardly at an angle of 15–35°, more preferably 15–25°. It will also be apparent that it is not necessary to restrict the initial opening of the package of region B, as such initial opening can be effected at either of side regions A or C. In that event, it is required to provide enough web material outside the line heat seal to permit the respective webs to be grasped.

Figure 12:
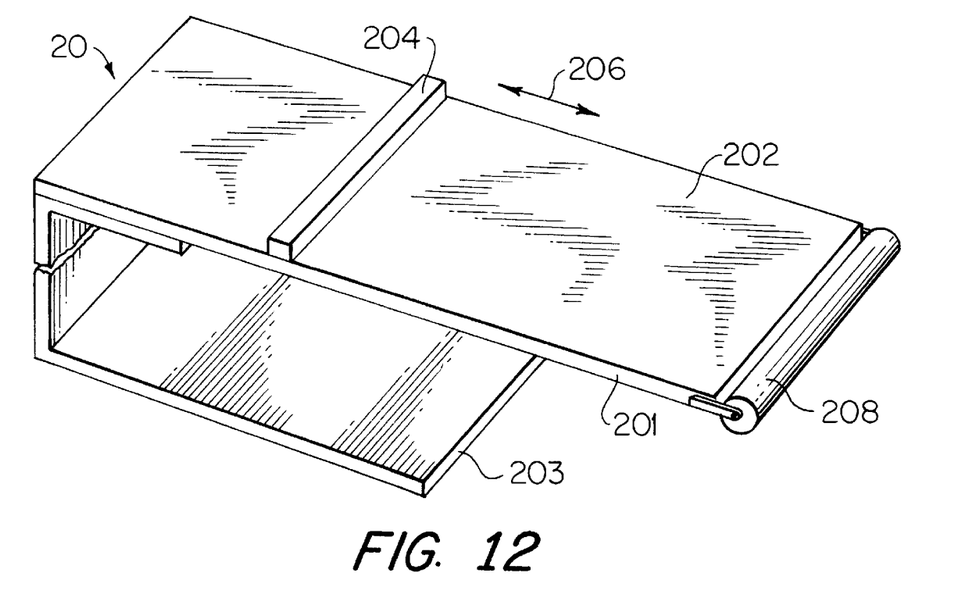
FIG. 12 is a diagrammatic perspective view of apparatus facilitating the insertion of an object to be sterilized into a pouch according to the invention.
Figure 13:
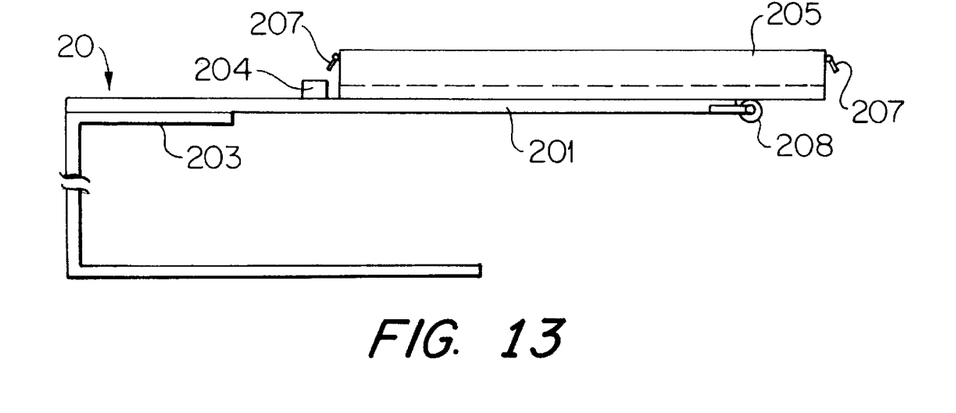
FIG. 13 is a diagrammatic side elevation view of the apparatus of FIG. 12.

Apparatus for facilitating the loading of a tray into a pouch in accordance with the invention is illustrated in FIGS. 12 and 13. Tray loading apparatus 20 includes an elongate cantilever table element 201 having a substantially flat planar upper surface 202 which is intended to be oriented such that surface 202 is oriented substantially horizontally for supporting an item, such as a loaded tray, to be inserted into a sterilization pouch. The apparatus also includes a cantilever support, such as U-shaped support member 203 for supporting table 201 in horizontal position. Support member 203 may include a clamp or the like (not shown) for securing the apparatus to the surface of a table or the like or for otherwise securely mounting the apparatus in fixed position. Surface 202 is preferably wider than the width of a tray to be inserted into the pouch. Table 201 includes an indicator 204 for indicating the position of a tray on surface 202 of the table. Indicator 204 is preferably a stop positioned to be abutted by the end of a tray 205 placed on the table. Stop 204 is preferably releasably secured to table 201 such that its position along the length of table 201 is adjustable in the direction of arrow 206 in order to accommodate trays of different size. In use, tray 205, bearing one or more items to be sterilized, is placed on surface 202 of table 201 with one of its ends abutting stop 204. Conventional trays of this type normally are provided with a handle 207 at each end to facilitate handling.

A sterilizable pouch of proper size for the object to be sterilized is then positioned to the right of loading device 20 with its access opening facing to the left, direction being in the sense of FIGS. 12 and 13. The top and intermediate webs forming the access opening to cavity 16 are separated, and the tubular pouch with its closed end to the right and with its open end to the left is moved to the left such that it is moved over and envelops table 201 and tray 205, thus positioning tray 205 in cavity 16 of the pouch, direction again being in the sense of FIGS. 12 and 13. Stop 204 is positioned on table 201 such that the tubular pouch is free to move (to the left is sense of FIGS. 12 and 13) sufficiently far beyond the object to be sterilized to enable the open end of the tubular pouch to be later sealed such that the object to be sterilized is reliably sealed within cavity 16. It will be apparent that indicator 204 need not be a stop and that various indicators may be employed. For example, table 201 could be provided with indicator marks for showing the proper positioning of trays of different size.

The pouch and trays are then removed together from table 201 to enable the pouch to be sealed. Since the pouch is flexible, removal can be effected manually by grasping the object despite the overlying web of the pouch. For example, handles at the end of a tray can be easily grasped through the overlying web of the pouch in this manner. After being removed from table 201, the pouch and tray are placed on a substantially horizontal surface and the pouch is then sealed as described above. The sealed pouch is then ready for sterilization.

Table 201 may be provided with a roller 208 mounted at its distal end to facilitate placement and removal of a heavy tray on the table. For this purpose, roller 208 is mounted such that its uppermost roller surface extends slightly above, in the sense of FIGS. 12 and 13, the plane of surface 202.

Preferred pouch packages in accordance with the invention are sterilizable in conventional high temperature sterilizing equipment in which steam sterilization is effected at a temperature of at least 270° F. for at least a three minute cycle. Preferred sterilizable pouches in accordance with the present invention withstand such sterilization conditions without impairment of the integrity of the heat seals or of the peelability of the delamination failure seal. In fact, peelability of the delamination failure peel seal is often enhanced by steam sterilization. Prior to such sterilization, there is a tendency, called for delamination in the failing web to extend inside the region of line heat seal 15. This tendency is generally less noticeable after steam sterilization. Preferably, pouches in accordance with the invention withstand steam sterilization at 270° F. for at least a 3 minute exposure phase and more preferably up to 10 minutes.

After steam sterilization, the pouch and object are removed from the autoclave and may be stored at ambient conditions to await use. Because the pouch webs are flexible, moving a pouch loaded with a heavy tray in and out of an autoclave is facilitated because the tray itself can be grasped through the pouch when the tray is completely sealed within the pouch. Shelf life of the sterilized pouch is comparable to that of a conventional wrapped tray and is at least 30 days.

Pouches in accordance with the invention are preferably made on pouch-forming machines which are of conventional design and which may be fully automated. It is preferred to form the line heat seals simultaneously in one or more heating steps. It is also preferred that the line heat seals 14 and 15 are superposed directly over one another as shown in the drawings. In that event, it is preferred to use two opposed heated platens to effect the line heat seals, one heated platen bearing against web 11 and the other heated platen bearing against web 13. It will be readily apparent, however, that the seals may be formed separately. For example, two webs may be heat sealed before the third web is added and heat sealed.

The invention is illustrated in the example which follows.

EXAMPLE

A plurality of pouch packages of the general type indicated in FIGS. 8–11 are fabricated by heat sealing three webs along a line heat seal in regions A, B and C. In each package, lower web 11' is "Securon", commercially available from the Fiberweb Group. The web is a drapable non-woven barrier fabric having a trilaminate structure with spunbonded polypropylene outer layers and an inner layer of melt blown polypropylene fibers, with a weight of 1.8 ounces per square yard. Web 11' is 16¾ inches in width and 30¾ inches in length. Intermediate web 12' is a three layer coextrusion having a bottom heat seal layer 121 for forming a permanent line heat seal 14 with the non-woven barrier fabric web, a top heat seal layer 123 for forming a permanent line heat seal 15 with upper web 13', and a core layer 122 bonded to heat seal layers 121 and 123 and which delaminates from upper heat seal layer 123 in the area of permanent line heat seal 15 when the heat-sealed package is peeled open. Bottom heat seal layer 121 is a blend of 50% by weight polypropylene (PPE) and 50 wt % polyisobutylene-modified (or rubber-modified) high density polyethylene (RMHDPE). Core layer 122 is RMHDPE (Paxon 3204), containing about 35% by weight of polyisobutylene. Upper heat seal layer 123 is PPE. Intermediate web 12' is provided with a grid pattern of perforations, each perforation being a circle having a diameter of ¼ inch, with the circles spaced about 2 inches lengthwise of the pouch and about 3½ inches across the width of the package. In the example, there are a total of 65 of the perforations. Web 11' extends outwardly about ½ inch beyond the end of intermediate web 12' forming flap portion 112' in web 11' as shown in FIG. 8. Webs 11' and 12' are in registry along their other three sides. Upper web 13' is a transparent tough adhesive lamination having a polypropylene heat seal layer 132 for forming a permanent line heat seal with heat seal layer 123 of intermediate web 12'. Layer 133 is 1 mil cast nylon. Layers 132 and 133 are adhesively bonded. Web 13' is shorter than webs 11' and 12' by about 1" at the chevron end of the package to facilitate peeling open of the sealed package and by about 1½ inches at the other end to form flap portion 127 in web 12'. The side edges of all three webs are in registry.

Permanent line heat seals 14 and 15 are then made in regions A, B and C using opposed heated platens for about 1 second at a pressure of about 300 psi with the upper platen at a temperature of about 330° F., and with the lower platen at a temperature of about 200°. Additional heat seals (not shown in the drawings) are also made between webs 11' and 12' at their outer ends so that the outer ends can be handled as a single web, thus facilitating insertion of an object before sterilization and opening of the pouch after sterilization. After formation of the permanent line heat seal, an acrylic cohesive substrate layer 105 ("Anchorbond 593") with release layer 108 is applied as shown in FIG. 10.

A stainless steel tray loaded with stainless steel medical instruments to be sterilized is then inserted into cavity 16 of the pouch through the access opening between webs 12' and 13', that is, through the open end of the pouch not having permanent line heat seals 14 and 15. The open end is then sealed as described above in connection with FIGS. 8–11. The sealed pouch is then autoclaved for 3 minutes with saturated steam for 3 minutes. After storage for 30 days at room temperature and at ambient relative humidity, the tray and instruments remain sterile.

After storage for 30 days, the packages are opened as described in connection with FIGS. 4–6 with little or no "webbing" occurring between layers 122 and 123 of intermediate web 12' in areas within the inner periphery of permanent line heat seal 15.

What is claimed is:

1. In a flexible, steam-sterilizable package having a cavity for enclosing an object to be sterilized, said cavity being openable by a peel seal for removal of a sterilized object from said cavity, said peel seal being formed between first and second flexible plastic webs, the improvement wherein:

one of said first and second plastic webs comprises a multi-layer web having a first heat sealable layer selected from the group consisting of polypropylene, polypropylene copolymers, and mixtures thereof, and a core layer bonded thereto selected from the group consisting of polyisobutylene-modified high density polyethylene (RMHDPE) and a blend of RMHDPE with polypropylene or polypropylene copolymer, and the other of said first and second plastic webs being heat sealed to the heat sealable layer of said multi-layer web by a permanent line heat seal;

the bond strength of said permanent line heat seal being stronger than the bond strength between said first heat sealable layer and said core layer of said multi-layer web, and the bond strength between said first heat sealable layer and said core layer of said multi-layer web being greater than the tear strength of said first heat sealable layer of said multi-layer web, whereby said peel seal comprises a delamination failure peel seal present between said first and second plastic webs in the region of at least a portion of said permanent line heat seal.

2. A flexible, steam sterilizable package according to claim 1 wherein said second plastic web is said multi-layer web and wherein said first plastic web is said other web.

3. A flexible, steam sterilizable package according to claim 2 wherein said first plastic web is transparent.

4. A flexible, steam sterilizable pouch package according to claim 3 wherein said first plastic web comprises a layer of a plastic and a heat sealable layer bonded thereto, said heat sealable layer of said first plastic web being bonded to said first heat sealable layer of said second plastic web by said permanent line heat seal.

5. A flexible, steam sterilizable package according to claim 1 wherein the heat sealable layers forming said permanent line heat seal are each the same and are each selected from the group consisting of polypropylene, polypropylene copolymers, and mixtures thereof.

6. A flexible, steam sterilizable package according to claim 4 wherein said plastic layer of said first plastic web is selected from the group consisting of nylon and polyester.

7. A flexible, steam sterilizable package according to claim 6 wherein said plastic layer of said first plastic web comprises cast nylon, said heat sealable layer of said first plastic web and said first heat sealable layer of said multi-layer web comprise polypropylene, said further heat sealable layer of said multi-layer web comprises a blend of polypropylene and polyisobutylene-modified polypropylene, and said core layer of said multi-layer web comprises polyisobutylene-modified polypropylene.

* * * * *